United States Patent

Main

[11] Patent Number: 5,246,965
[45] Date of Patent: Sep. 21, 1993

[54] ARYLETHERS, THEIR MANUFACTURE AND METHODS OF TREATMENT
[75] Inventor: Alan J. Main, Basking Ridge, N.J.
[73] Assignee: Ciba-Geigy, Ardsley, N.Y.
[21] Appl. No.: 947,652
[22] Filed: Sep. 17, 1992

Related U.S. Application Data

[63] Continuation-in-part of Ser. No. 714,109, Jun. 11, 1991, abandoned.
[51] Int. Cl.$^5$ ............... A61K 31/155; C07C 257/18
[52] U.S. Cl. .................... 514/532; 514/546; 514/554; 514/562; 514/567; 514/595; 514/604; 514/605; 514/613; 514/617; 514/630; 514/637; 560/105; 560/138; 562/114; 562/426; 562/427; 562/440; 564/47; 564/52; 564/56; 564/80; 564/92; 564/99; 564/123; 564/182
[58] Field of Search ............... 560/105, 138; 562/114, 562/426, 427, 440; 564/47, 52, 56, 80, 92, 99, 123, 182, 189, 270; 514/532, 546, 554, 562, 567, 595, 596, 604, 605, 613, 617, 630

[56] References Cited

U.S. PATENT DOCUMENTS

| | | | |
|---|---|---|---|
| 4,034,401 | 7/1977 | Hamane et al. | 260/564 |
| 4,324,794 | 4/1982 | Tidwell et al. | 424/273 |
| 4,808,604 | 2/1989 | Beck et al. | 514/381 |
| 4,933,347 | 6/1990 | Tidwell et al. | 514/256 |
| 4,940,723 | 7/1990 | Tidwell et al. | 514/396 |
| 4,963,589 | 10/1990 | Tidwell et al. | 514/636 |

FOREIGN PATENT DOCUMENTS

| | | |
|---|---|---|
| 0150118 | 7/1985 | European Pat. Off. |
| 276064 | 7/1988 | European Pat. Off. |
| 0366066 | 5/1990 | European Pat. Off. |

OTHER PUBLICATIONS

J. Med. Chem. 21, 1132 (1978).
J. Assoc. Off. Anal. Chem. 69, 624 (1986).
Chem. Abst. 115, 788f (1991).
J. Med. Chem. 16, 970 (1973).
J. Med. Chem. 18, 477 (1975).
J. Med. Chem. 19, 634 (1976).
J. Med. Chem. 10, 1123 (1967).
J. Med. Chem. 11, 245 (1968).
J. Med. Chem. 12, 112 (1969).
NTIS Application PB-237538 (1990).

Primary Examiner—Richard L. Raymond
Attorney, Agent, or Firm—Norbert Gruenfeld

[57] ABSTRACT

The invention relates to the compounds of the formula

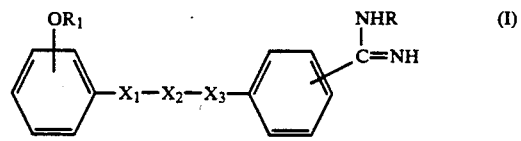

wherein the C(=NH)—NHR group may be in tautomeric or isomeric form, and pharmaceutically acceptable salts thereof, in which:

R is hydrogen or an acyl radical which is derived from an organic carbonic acid, an organic carboxylic acid, a sulfonic acid, or a carbamic acid;

$R_1$ is a substituent selected from an aliphatic hydrocarbon radical, an araliphatic hydrocarbon radical and a cycloaliphatic hydrocarbon radical;

$X_1$ and $X_3$, independently of one another, are oxygen (—O—) or sulphur (—S—); and $X_2$ is a divalent aliphatic hydrocarbon radical which may be interrupted by an aromatic radical; wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic, araliphatic or cycloaliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic, araliphatic or cycloaliphatic alcohol or which is esterified by an aliphatic or araliphatic carboxylic acid; and wherein a cycloaliphatic hydrocarbon radical may be substituted by an aliphatic radical. The compounds are useful as selective LTB$_4$ receptor antagonists in the treatment of conditions or syndromes in mammals which are responsive to LTB$_4$ receptor antagonism.

21 Claims, No Drawings

ARYLETHERS, THEIR MANUFACTURE AND METHODS OF TREATMENT

CROSS REFERENCE TO RELATED APPLICATIONS

This application is a continuation-in-part of application Ser. No. 714,109 filed Jun. 11, 1991, now abandoned.

SUMMARY OF THE INVENTION

The invention relates to the phenoxyalkoxyphenyl derivatives and thio analogs as defined herein which are particularly useful as selective Leukotriene B$_4$ (LTB$_4$) receptor antagonists, methods for preparation thereof, pharmaceutical compositions comprising said compounds, and a method of antagonizing LTB$_4$ and of treating conditions or syndromes in mammals which are responsive to LTB$_4$ antagonism using said compounds or pharmaceutical compositions comprising said compounds of the invention.

Leukotriene B$_4$ (LTB$_4$) is an important inflammatory mediator being a potent chemotactic agent and activator of polymorphonuclear leucocytes (PMN's) and monocytes. It modulates the production and effects of other important inflammatory mediators e.g. Interleukin-1 and gamma interferon. LTB$_4$ has been implicated in the pathogenesis of a number of inflammatory diseases, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma.

There is a strong need in the art in finding potent antagonists of LTB$_4$ on human PMN's, especially those which are orally active. It has been found that the compounds according to the present invention exhibit significant LTB$_4$ antagonistic activity on human PMN's and are orally active.

The compounds of the present invention are useful for the treatment of the conditions mediated by LTB$_4$ which are cited above. In addition the compounds are also useful for the treatment of pain and osteoarthritis, and for the treatment of ocular conditions, such as ocular allergy and inflammation.

DETAILED DESCRIPTION OF THE INVENTION

The invention relates to phenoxyalkoxyphenyl derivatives and thio analogs of the formula

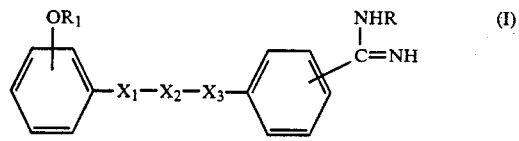

wherein the C(=NH)—NHR group may be in tautomeric or isomeric form, and pharmaceutically acceptable salts thereof, in which:

R is hydrogen or an acyl radical which is derived from an organic carbonic acid, an organic carboxylic acid, a sulfonic acid, or a carbamic acid;

R$_1$ is a substituent selected from an aliphatic hydrocarbon radical, an araliphatic hydrocarbon radical and a cycloaliphatic hydrocarbon radical;

X$_1$ and X$_3$, independently of one another, are oxygen (—O—) or sulphur (—S—); and X$_2$ is a divalent aliphatic hydrocarbon radical which may be interrupted by an aromatic radical; wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic, araliphatic or cycloaliphatic alcohol or which is esterified by an aliphatic or araliphatic carboxylic acid;

wherein a cycloaliphatic hydrocarbon radical may be substituted by an aliphatic radical; which are particularly useful as selective LTB$_4$ antagonists, methods for preparation thereof, pharmaceutical compositions comprising said compounds, and a method of antagonizing LTB$_4$ and of treating diseases in mammals which are responsive to LTB$_4$ antagonism using said compounds or pharmaceutical compositions comprising said compounds of the invention.

As the compounds according to the invention have a basic centre, they can thus form acid addition salts, especially pharmaceutically acceptable salts. There are formed, for example, with inorganic acids, such as mineral acids, for example sulfuric acid, a phosphoric or hydrohalic acid, or with organic carboxylic acids, such as (C$_1$-C$_4$-)alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as (C$_1$-C$_4$-)alkane- or arylsulfonic acids which are unsubstituted or substituted, for example, by halogen, for example methane- or toluenesulfonic acid. Preferred are salts formed with hydrochloric acid, methanesulfonic acid and maleic acid.

An acyl radical which is derived from an organic carbonic acid is, for example, alkoxycarbonyl or alkenyloxycarbonyl which in each case are unsubstituted or substituted by an aromatic radical or is cycloalkoxycarbonyl which unsubstituted or substituted by lower alkyl.

An acyl radical which is derived from an organic carboxylic acid is, for example, lower alkanoyl, phenyl-lower alkanoyl or unsubstituted or substituted aroyl, such as benzoyl, naphthoyl, indanoyl or fluorenoyl.

An acyl radical which is derived from a sulfonic acid is, for example, alkanesulfonyl, arylalkanesulfonyl, cycloalkanesulfonyl or arylsulfonyl.

An acyl radical which is derived from a carbamic acid is, for example, amino-carbonyl which is substituted by alkyl, arylalkyl or aryl.

An aromatic radical is, for example, unsubstituted or substituted such as monosubstituted or polysubstituted, for example, disubstituted or secondarily trisubstituted, carbocyclic aryl, such as phenyl, naphthyl, indanyl or fluorenyl.

An aliphatic hydrocarbon radical is, for example, lower alkyl, lower alkenyl and secondarily lower alkynyl.

An araliphatic hydrocarbon radical is, for example, optionally substituted phenyl-lower alkyl and secondarily phenyl-lower alkenyl and phenyl-lower alkynyl.

A cycloaliphatic hydrocarbon radical is, for example, cycloalkyl and secondarily cycloalkenyl, which is unsubstituted or mono- or polysubstituted, for example, disubstituted, by lower alkyl. A cycloaliphatic hydrocarbon radical is also optionally substituted cycloalkyl-lower alkyl.

A divalent aliphatic hydrocarbon radical is, for example, lower alkylene.

A divalent aliphatic hydrocarbon radical which is interrupted by an aromatic radical is, for example, lower alkylene-phenylene-lower alkylene or lower alkylene-naphthylene-lower alkylene.

An aliphatic alcohol is, for example, a lower alkanol or lower alkenol, and an araliphatic alcohol is, for example, a phenyl-lower alkanol.

Hydroxy which is etherified by an aliphatic, cycloaliphatic or araliphatic alcohol is, for example, lower alkoxy or lower alkenyloxy, cyclohexyl-lower alkoxy, and phenyl-lower alkoxy.

An aliphatic carboxylic acid is, for example, a lower alkanoic or lower alkenoic acid, and an araliphatic carboxylic acid is, for example, a phenyl-lower alkanoic acid.

Hydroxy which is esterified by an aliphatic or araliphatic carboxylic acid is, for example, lower alkanoyloxy, secondarily lower alkenoyloxy, or is phenyl-lower alkanoyloxy.

The phenyl rings of formulae I and IA as well as aromatic radicals referred to before and hereafter are generally unsubstituted or further substituted such as monosubstituted or polysubstituted, for example disubstituted or secondarily trisubstituted, in particular, for example, by a substituent selected from the group consisting of halogen, trifluoromethyl, lower alkyl, lower alkenyl, lower alkynyl, hydroxy, lower alkoxy, lower alkenyloxy, cyclohexyl-lower alkoxy, phenyl-lower alkoxy, lower alkanoyloxy, lower alkenoyloxy, and phenyl-lower alkanoyloxy. Preferably, the phenyl rings of formula I and IA do not exhibit any additional substitutent.

Preferred positions of the following structural elements in the corresponding phenyl ring in formula I are: position 2 (ortho) for —O—$R_1$ of the corresponding phenyl ring with respect to —$X_1$—, position 4 (para) for —C(=NH)—NHR— of the corresponding phenyl ring with respect to —$X_3$—.

The substituent R being acyl may be located on either nitrogen of the —C(=NH)NH$_2$ grouping; both forms are encompassed by the instant invention.

The term "substituted by one or more substituents" refers preferably to one, two or three such substituents, advantageously one or two.

The general definitions used above and below have, if not defined differently, the following meanings:

The expression "lower" means that corresponding groups and compounds in each case contain in particular not more than 7, preferably not more than 4, carbon atoms.

Alkoxycarbonyl is, in particular, $C_2$-$C_{12}$-alkoxycarbonyl and is, for example, methoxy-, ethoxy-, propyloxy- pivaloyloxy- or octyloxy-carbonyl. $C_2$-$C_9$-Alkoxycarbonyl is preferred.

Alkenyloxycarbonyl is, in particular, $C_3$-$C_{12}$-alkenyloxycarbonyl, for example, allyloxycarbonyl. Preferred is $C_3$-$C_5$-alkenyloxycarbonyl.

Cycloalkyloxycarbonyl is, in particular, $C_3$-$C_7$-cycloalkoxycarbonyl, preferred is cyclopentyloxycarbonyl or cyclohexyloxycarbonyl.

Lower alkanoyl is, in particular, $C_1$-$C_7$-alkanoyl and is, for example, formyl, acetyl, propionyl, butyryl, isobutyryl or pivalolyl. $C_2$-$C_5$-Alkanoyl is preferred.

Phenyl-lower alkanoyl is, in particular, phenyl-$C_2$-$C_7$-alkanoyl and is, for example, phenylacetyl or 2- or 3-phenylpropionyl. Phenyl-$C_2$-$C_4$-alkanoyl is preferred.

Naphthoyl is 1- or 2-naphthoyl.

Indanoyl is, for example, 1-, 2-, 3- or 4-indanoyl.

Fluorenoyl is, for example, 1-, 2-, 3-, 4- or 5-fluorenoyl.

Alkanesulfonyl is, in particular, $C_1$-$C_7$alkanesulfonyl and is, for example, methane-, ethane-, n-propane- or isopropanesulfonyl. $C_1$-$C_4$-Alkanesulfonyl is preferred.

Arylalkanesulfonyl is, in particular, phenyl-$C_1$-$C_7$alkanesulfonyl, for example, benzyl-or 1- or 2-phenylethan-sulfonyl. Phenyl-$C_1$-$C_4$-alkane-sulfonyl is preferred.

Cycloalkanesulfonyl is, in particular, $C_3$-$C_7$-cycloalkanesulfonyl, preferred is cyclopentanesulfonyl or cyclohexanesulfonyl.

Naphthyl is 1- or 2-naphthyl.

Indanyl is, for example, 1-, 2-, 3- or 4-indanyl.

Fluorenyl is, for example, 1-, 2-, 3-, 4- or 5-fluorenyl.

Lower alkyl is, in particular, $C_1$-$C_7$-alkyl and is, for example, methyl, ethyl, n-propyl, isopropyl, n-butyl, isobutyl, sec-butyl, tert-butyl and furthermore includes corresponding pentyl, hexyl and heptyl radicals. $C_1$-$C_4$-Alkyl is preferred.

Lower alkenyl is, in particular, $C_3$-$C_7$-alkenyl and is, for example, 2-propenyl or 1-, 2-or 3-butenyl. $C_3$-$C_5$-Alkenyl is preferred.

Lower alkynyl is, in particular, $C_3$-$C_7$-alkynyl and is preferably propargyl.

Phenyl-lower alkyl is, in particular ,phenyl-$C_1$-$C_4$-alkyl and is preferably benzyl, 1- and 2-phenethyl, while phenyl-lower alkenyl and phenyl-lower alkynyl are, in particular, phenyl-$C_2$-$C_5$alkenyl and -alkynyl, in particular 2-phenyl-vinyl, 3-phenylallyl and 3-phenylpropargyl.

Cycloalkyl is, in particular, $C_3$-$C_7$-cycloalkyl and is, for example, cyclopropyl, cyclobutyl, cyclopentyl, cyclohexyl and cycloheptyl. Cyclopentyl and cyclohexyl are preferred.

Cycloalkenyl is, in particular, $C_3$-$C_7$-cycloalkenyl and is preferably cyclopent-2- or -3-enyl, or cyclohex-2- and -3-en-yl.

Lower alkylene e.g. in amino which is disubstituted by lower alkylene is, in particular, $C_2$-$C_6$-alkylene and is, for example, butylene, pentylene, or 2,6-butylene. Preferred is $C_4$-$C_5$-alkylene, especially pentylene.

Lower alkylene ($X_2$) is, in particular, $C_2$-$C_8$-alkylene, preferably straight-chain, and is, for example, ethylene, propylene, butylene, pentylene, hexylene, pentylene and also octylene. $C_4$-$C_7$-Alkylene is preferred, especially pentylene and also butylene, hexylene or heptylene.

Lower alkylene which is interrupted by a phenyl radical ($X_2$) is, in particular, lower alkylene-phenylene-lower alkylene or lower alkylene-naphthylene-lower alkylene such as $C_2$-$C_4$-alkylene-phenylene-$C_2$-$C_4$-alkylene or $C_2$-$C_4$-alkylene-naphthylene-$C_2$-$C_4$-alkylene, preferably straight-chain, and is, for example, methylene-phenylene-methylene, 1,2-ethylene-phenylene-1,2-ethylene, such as 1,2-ethylene-1,4-phenylene-1,2-ethylene, 1,3-propylene-phenylene-1,3-propylene, such as 1,3-propylene-1,4-phenylene-1,3-propylene, or butylene-phenylene-butylene radicals, also a corresponding 1,2-ethylene-naphthylene-1,2-ethylene radical. $C_2$–$C_4$-alkylene-phenylene-$C_2$–$C_4$-alkylene or $C_2$–$C_3$-alkylene-naphthylene-$C_2$–$C_3$-alkylene is preferred, especially 1,2-ethylene-1,4-phenylene-1,2-ethylene.

Halogen is, in particular, fluorine, chlorine or bromine, and furthermore includes iodine.

Lower alkoxy is, in particular, $C_1$–$C_7$-alkoxy and is, for example, methoxy, ethoxy, n-propyloxy, isopropyloxy, n-butyloxy, isobutyloxy, sec-butyloxy, tert-butyloxy and furthermore includes corresponding pentyloxy, hexyloxy and heptyloxy radicals. $C_1$–$C_4$-Alkoxy is preferred.

Lower alkenyloxy is, in particular, $C_3$–$C_7$-alkenyloxy and is, for example, allyloxy or but-2-en- or but-3-enyloxy. $C_3$–$C_5$-Alkenyloxy is preferred.

Phenyl-lower alkoxy is, in particular, phenyl-$C_1$–$C_4$-alkoxy, such as benzyloxy, 1- or 2-phenylethoxy, or 1-, 2- or 3-phenylpropyloxy.

Lower alkanoyloxy is, in particular, $C_2$–$C_8$-alkanoyloxy, in particular, $C_2$–$C_5$-alkanoyloxy, such as acetyloxy, propionyloxy or pivaloyoxy.

Lower alkenoyloxy is, in particular, $C_3$–$C_8$-alkenoyloxy, in particular, $C_3$–$C_5$-alkenoyloxy, such as propenoyloxy.

Phenyl-lower alkanoyloxy is, in particular, phenyl-$C_2$–$C_8$-alkanoyloxy, in particular, phenyl-$C_2$–$C_5$-alkanoyloxy, such as phenylacetyloxy, phenylpropionyloxy or phenylpivaloyloxy.

The compounds of the invention exhibit valuable pharmacological properties in mammals, and are particularly useful as selective Leukotriene B4 ($LTB_4$) receptor antagonists, e.g. for the treatment of a condition or syndrome in a mammal responsive to the selective antagonism of $LTB_4$ receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma. The compounds of the invention are also useful as analgesics for the treatment of pain, of any origin, and for the treatment of osteoarthritis.

The above-cited properties are demonstrable in in vitro and in vivo tests, using advantageously mammals, e.g. rats. Said compounds can be applied in vitro in the form of solutions, e.g. preferably aqueous solutions, and in vivo either enterally or parenterally, advantageously orally, e.g. as a suspension or in aqueous solution. The dosage in vitro may range between about 0.5 ng/ml and about 100 ng/ml. The dosage in vivo may range, depending on the route of administration, between about 1 and about 1000 mg/kg per day.

Beneficial effects are evaluated in pharmacological tests generally known in the art, e.g. as illustrated herein.

Receptor Binding with [$^3$H]-$LTB_4$ to Intact Human Neutrophils:

Neutrophils (PMN's) are prepared from uncoagulated human venous blood. Blood is dispersed into 50 ml polypropylene tubes containing 15 ml of HESPAN (Dupont, Wilmington, Del.), and mixed. Tubes are allowed to stand at room temperature for 40 minutes until most of the red blood cells sediment. The supernatants are removed and centrifuged for 5–10 min at $400 \times$ g. The remaining pellets are diluted in 70 ml of Phosphate Buffered Saline without calcium and magnesium (PBS without metals; GIBCO, Grand Island, N.Y.) and 35 ml of this suspension are placed in each of two polypropylene tubes containing 15 ml of Ficoll-Paque (Sigma, St. Louis, Mo.). Gradients are then centrifuged for 15 minutes at $420 \times$ g. The mononuclear cell layer is discarded and the remaining red blood cell pellet is resuspended in 10 ml of PBS without metals. Twenty ml of filtered deionized water are added to the suspension for approximately 20 sec followed by the same volume of buffer at two times the normal concentration. The cell suspension is mixed and centrifuged for 5 min at $200 \times$ g, followed by one wash with buffer, and final resuspension.

Binding of [$^3$H]$LTB_4$ to $LTB_4$ receptors is measured in intact human polymorphonuclear leukocytes, as described by Gorman and Lin (Gorman, R. and Lin, A Methods Enzymol. 141:372–378, 1987). Intact human neutrophils are suspended in Hank's Balanced Salt Solution (HBSS) at a concentration of $3 \times 10^6$ cells/assay tube. An aliquot of the cell suspension (300 µl) is added to triplicate tubes containing 50 µl [$^3$H]$LTB_4$ (specific activity 32 Ci/mmol, DuPont-NEN, Boston, Mass.) at a final concentration of 0.5 nM, 100 µl buffer and 50 µl drug or buffer. Nonspecific binding is determined in the presence of 300 nM $LTB_4$. The reaction is initiated by addition of cell suspension and continued at 0° C. for 20 min. Bound radioactivity is isolated by vacuum filtration through Whatman GF/C glass fiber filters using a Brandel cell harvester and unbound radioactivity removed with $2 \times 5$ ml washes with ice-cold saline. Filters are placed in polyethylene scintillation mini-vials to which is added 3.5 ml of Formula-989 scintillation cocktail (NEN). After equilibration, radioactivity determinations and data calculations are performed using non-linear regression analysis on RS/1.

$LTB_4$-Induced PMN Aggregation

Human PMNs are prepared as previously described. Neutrophil aggregation is assessed by monitoring the intensity of light passing through a suspension of cells (Craddock et al., J. Clin. Invest. 60: 260–264, 1977) using a Payton dual channel aggregometer (model 300BD). Cuvettes containing 0.25 ml of cell suspension ($25 \times 10^6$ cells/ml) in PBS without calcium and magnesium are incubated with 5 µg/ml ml of cytochalasin B for 2 minutes at 37° C. 5 µl of 2 µM $LTB_4$ in PBS (20 nM final concentration) are added and the aggregation response monitored for 3–5 min, the time required for optimal response. Compounds are solubilized in 0.01M DMSO and then diluted in PBS to 0.001M. 5 µl of compound solution is added along with cytochalasin B and cells as described above. Following the preincubation period 5 µl of 2 µM $LTB_4$ are added and aggregation is measured. Percent inhibition of aggregation is calculated by comparing peak heights in the presence and absence of compound. Percent inhibition is plotted as a function of the log concentration of compound and the $IC_{50}$ determined directly from the graph.

$LTB_4$-Induced Neutropenia in the Rat

Male Sprague Dawley rats (crl: CDBR, Charles River, Wilmington, Mass.) (250–300) grams are fasted overnight prior to the experiment. At least six animals are used per treatment group. Rats are given vehicle or compound either intravenously or orally and at intervals after dosing, neutrophil counts are determined from blood samples obtained just prior to and 20 seconds after intravenous infusion of 200 ng $LTB_4$. In studies are compound is administered orally, drug is given by gavage. When drug is administered intravenously, rats are first anesthetized with 50 mg/kg i.p. of Sodium Pentabarbital. The jugular vein is exposed and cleaned of the surrounding tissue. At 3, 4 or 18 hours following administration of compound or vehicle by either route, blood samples are taken (0.3 ml of blood in 1.5 ml polypropylene microcentrifuge tube containing 0.01 ml 7.5% EDTA). Blood neutrophil counts are determined using a Technicon H-1 hematology instrument. Antagonism of the $LTB_4$-induced neutropenia response for the compounds tested is calculated.

Analgesic activity can be demonstrated e.g. in the Randall-Selitto test for analgesia, e.g. as described in Arch. Int. Pharmacodyn. Ther. 111, 409 (1957).

Antiinflammatory activity can be demonstrated by measuring the inhibition of the edema and inhibition of the influx of polymorphonuclear (PMN's) and mononuclear leukocytes (monocytes and macrophages) after oral administration in the rat model in which pleurisy is first induced by injecting carrageenin into the pleural cavity, e.g. according to A. P. Almeida et al., J. Pharmacol. Exp. Therap. 214, 74 (1980).

Bronchial effects such as anti-asthmatic activity, can be demonstrated in the antigen-induced guinea pig bronchoconstriction test, e.g. as described by Anderson et al, Br. J. Pharmacol. 1983, 78, 67-74.

The trinitrobenzenesulfonic acid-induced chronic colitis test in the rat, e.g. as described by Wallace et al, Gastroenterology 1989, 96, 29-36, can be used to evaluate compounds for effects indicative of utility in inflammatory bowel diseases.

The arachidonic acid-induced mouse ear edema test, e.g. as described by Young et al, J. Invest, Dermatol. 1984, 82, 367-371 can be used to evaluate compounds for effects indicative of utility in dermatological disorders such as psoriasis.

The invention especially relates to compounds of formula I and pharmaceutically acceptable salts thereof, in which:

R is hydrogen, ($C_1$-$C_{12}$-)alkoxycarbonyl or ($C_2$-$C_{12}$-)alkenyloxycarbonyl, each of which is unsubstituted or substituted by phenyl, naphthyl, indanyl or fluorenyl, or is ($C_3$-$C_7$-)cycloalkoxycarbonyl being unsubstituted or mono- or polysubstituted by lower alkyl, or is lower alkanoyl or phenyl-lower alkanoyl, or is benzoyl, naphthoyl, indanoyl or fluorenoyl, or is ($C_1$-$C_7$-)alkanesulfonyl, phenyl-($C_1$-$C_7$-)alkanesulfonyl, ($C_3$-$C_7$-)cycloalkanesulfonyl, or phenylsulfonyl, or is aminocarbonyl which is substituted by lower alkyl, phenyl-lower alkyl or phenyl;

$R_1$ is lower alkyl, lower alkenyl, lower alkynyl, phenyl-lower alkyl, phenyl-lower alkenyl, phenyl-lower alkynyl, ($C_3$-$C_7$-)cycloalkyl, ($C_3$-$C_7$-)cycloalkenyl, ($C_3$-$C_7$)-cycloalkyl-lower alkyl or ($C_3$-$C_7$)-cycloalkenyl-lower alkyl;

$X_1$ and $X_3$, independently of one another, are O or S;

$X_2$ is lower alkylene, lower alkylene-phenylene-lower alkylene or lower alkylene-naphthylene-lower alkylene;

wherein the phenyl rings of formula I may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, cyclohexyl-lower alkoxy, lower alkanoyloxy, lower alkenoyloxy and phenyl-lower alkanoyloxy; wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, cyclohexyl-lower alkoxy, lower alkanoyloxy, lower alkenoyloxy and phenyl-lower alkanoyloxy.

The invention especially relates to compounds of formula I and pharmaceutically acceptable salts thereof, in which:

R is hydrogen, $C_1$-$C_{12}$-alkoxy-carbonyl, $C_2$-$C_5$-alkanoyl, phenyl-$C_2$-$C_5$-alkanoyl, benzoyl which is unsubstituted or substituted by halogen, trifluoromethyl, $C_1$-$C_7$-alkyl, or $C_1$-$C_7$-alkoxy, $C_3$-$C_6$-cycloalkylcarbonyl which is unsubstituted or substituted by $C_1$-$C_7$-alkyl, or is benzoyl, naphthoyl, indanoyl or fluorenoyl, or is $C_1$-$C_7$-alkanesulfonyl, phenyl-$C_1$-$C_7$-alkanesulfonyl, $C_3$-$C_7$-cycloalkanesulfonyl, or phenylsulfonyl, or is aminocarbonyl which is substituted by $C_1$-$C_7$-alkyl, phenyl-$C_1$-$C_7$-alkyl or phenyl;

$R_1$ is $C_1$-$C_7$-alkyl, phenyl-$C_1$-$C_7$-alkyl, $C_3$-$C_6$-cycloalkyl, and $C_3$-$C_6$-cycloalkyl-lower alkyl;

$X_1$ and $X_3$ each are —O—, or furthermore are, independently of one another, —O— or —S—;

$X_2$ is $C_2$-$C_7$-alkylene or $C_2$-$C_4$-alkylene-phenylene-$C_2$-$C_4$-alkylene;

wherein phenyl in the above definitions is unsubstituted or, furthermore, independently of one another, substituted by a substituent selected from halogen, trifluoromethyl, $C_1$-$C_7$-alkyl, and $C_1$-$C_7$-alkoxy.

The invention especially relates to compounds of formula I and pharmaceutically acceptable salts thereof, in which —O—$R_1$ is located in position 2 (ortho) of the corresponding phenyl ring with respect to —$X_1$—; and —C(=NH)—NH—R is located in position 4 (para) of the corresponding phenyl ring with respect to —$X_3$—.

The invention especially relates to compounds of formula IA

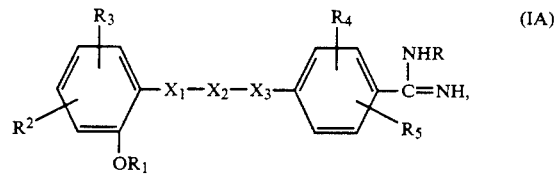

wherein the C(=NH)—NHR group may be in tautomeric or isomeric form, and pharmaceutically acceptable salts thereof, in which:

R is hydrogen, $C_1$-$C_{12}$-alkoxycarbonyl, such as methoxycarbonyl or octyloxycarbonyl, phenyl-$C_1$-$C_4$-alkoxycarbonyl, such as benzyloxycarbonyl, $C_2$-$C_5$-alkanoyl, such as acetyl, benzoyl which is unsubstituted or substituted by halogen, trifluoromethyl, $C_1$-$C_4$-alkyl, or $C_1$-$C_4$-alkoxy, such as 3,4-dimethoxybenzoyl, $C_3$-$C_6$-cycloalkylcarbonyl which is unsubstituted or substituted by $C_1$-$C_4$-alkyl, such as 2-isopropyl-5-methyl-cyclohexylcarbonyl; $R_1$ is $C_1$-$C_4$-alkyl, such as methyl, ethyl or isopropyl, phenyl-$C_1$-$C_4$-alkyl, such as benzyl, $C_3$-$C_6$-cycloalkyl, such as cyclohexyl;

$R_2$, $R_3$, $R_4$ and $R_5$, independently of one another, are hydrogen, halogen, such as fluoro, chloro or bromo, $C_1-C_4$-alkoxy, such as methoxy, or $C_1-C_4$-alkyl, such as methyl, phenyl-$C_1-C_4$-alkoxy, such as benzyloxy, or $C_3-C_6$-cycloalkyl-$C_1-C_4$-alkoxy, such as cyclohexylmethoxy;

$X_1$ and $X_3$ are —O—;

$X_2$ is $C_4-C_7$-alkylene, such as pentylene, or $C_2-C_4$-alkylene-phenylene-$C_2-C_4$-alkylene, such as 1,2-ethylene-1,4-phenylene-1,2-ethylene.

The invention especially relates to compounds of formula IA and pharmaceutically acceptable salts thereof, in which:

R is hydrogen;

$R_1$ is $C_1-C_4$-alkyl, such as methyl or isopropyl, phenyl-$C_1-C_4$-alkyl, such as benzyl, $C_3-C_6$-cycloalkyl, such as cyclohexyl;

$R_2$, $R_3$, $R_4$ and $R_5$, independently of one another, are hydrogen, halogen, such as fluoro, chloro or bromo, $C_1-C_4$-alkoxy, such as methoxy, or $C_1-C_4$-alkyl, such as methyl;

$X_1$ and $X_3$ are —O—;

$X_2$ is $C_4-C_7$-alkylene, such as pentylene, or $C_2-C_4$-alkylene-phenyl-$C_2-C_4$-alkylene, such as 1,2-ethylene-1,4-phenylene-1,2-ethylene.

The invention especially relates to compounds of formula IA and pharmaceutically acceptable salts thereof, in which:

R is $C_1-C_4$alkanesulfonyl, such as methane-, ethane- or isopropanesulfonyl, phenyl-$C_1-C_4$-alkanesulfonyl, such as benzylsulfonyl, $C_3-C_7$-cycloalkane-sulfonyl, such as cyclohexanesulfonyl, or phenylsulfonyl, or is aminocarbonyl which is substituted by $C_1-C_4$-alkyl, phenyl-$C_1-C_4$-alkyl or phenyl;

$R_1$ is $C_1-C_4$-alkyl, such as methyl or isopropyl, phenyl-$C_1-C_4$-alkyl, such as benzyl, $C_3-C_6$-cycloalkyl, such as cyclohexyl;

$R_2$, $R_3$, $R_4$ and $R_5$, independently of one another, are hydrogen, halogen, such as fluoro, chloro or bromo, $C_1-C_4$-alkoxy, such as methoxy, or $C_1-C_4$-alkyl, such as methyl;

$X_1$ and $X_3$ are —O—;

$X_2$ is $C_4-C_7$-alkylene, such as pentylene, or $C_2-C_4$-alkylene-phenyl-$C_2-C_4$-alkylene, such as 1,2-ethylene-1,4-phenylene-1,2-ethylene.

The invention further especially relates to compounds of formula IA and pharmaceutically acceptable salts thereof, in which:

R is $C_1-C_{12}$-alkoxycarbonyl, such as methoxycarbonyl or octyloxycarbonyl, phenyl-$C_1-C_4$-alkoxycarbonyl, such as benzyloxycarbonyl, $C_2-C_5$-alkanoyl, such as acetyl, benzoyl which is unsubstituted or substituted by halogen, trifluoromethyl, $C_1-C_4$-alkyl, or $C_1-C_4$-alkoxy, such as 3,4-dimethoxybenzoyl, $C_3-C_6$-cycloalkylcarbonyl which is unsubstituted or substituted by $C_1-C_4$-alkyl, such as 2-isopropyl-5-methylcyclohexylcarbonyl;

$R_1$ is $C_1-C_4$-alkyl, such as methyl or isopropyl, or phenyl-$C_1-C_4$-alkyl, such as benzyl;

$R_2$ is hydrogen or halogen, such as fluoro, $C_1-C_4$-alkoxy, such as methoxy;

$R_3$ is hydrogen or halogen, such fluoro;

$R_4$ and $R_5$, independently of one another, are hydrogen, halogen, such as fluoro, or $C_1-C_4$-alkoxy, such as methoxy;

$X_1$ and $X_3$ are —O—;

$X_2$ is $C_4-C_7$-alkylene, especially pentylene.

The invention further especially relates to compounds of formula IA and pharmaceutically acceptable salts thereof, in which:

R is hydrogen;

$R_1$ is $C_1-C_4$-alkyl, such as methyl or isopropyl, or phenyl-$C_1-C_4$-alkyl, such as benzyl;

$R_2$ is hydrogen or halogen, such as fluoro, $C_1-C_4$-alkoxy, such as methoxy;

$R_3$ is hydrogen or halogen, such fluoro;

$R_4$ and $R_5$, independently of one another, are hydrogen, halogen, such as fluoro, or $C_1-C_4$-alkoxy, such as methoxy;

$X_1$ and $X_3$ are —O—;

$X_2$ is $C_4-C_7$-alkylene, especially pentylene.

The invention further especially relates to compounds of formula IB

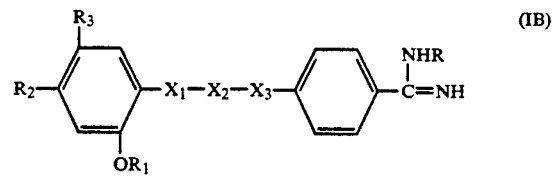

(IB)

wherein the C(=NH)—NHR group may be in tautomeric or isomeric form, and pharmaceutically acceptable salts thereof, in which:

R is hydrogen;

$R_1$ is $C_1-C_4$-alkyl, such as methyl or isopropyl;

$R_2$ is hydrogen, halogen, such as fluoro, or $C_1-C_4$-alkoxy, such as methoxy;

$R_3$ is hydrogen or halogen, such as fluoro;

$X_1$ and $X_3$ are —O—;

$X_2$ is $C_4-C_7$-alkylene, especially pentylene.

The invention further especially relates to compounds of formula (IB) and pharmaceutically acceptable salts thereof, in which:

R is hydrogen;

$R_1$ is $C_1-C_4$-alkyl, such as methyl or isopropyl; $R_2$ and $R_3$, independently of one another, are hydrogen or halogen, such as fluoro;

$X_1$ and $X_3$ are —O—;

$X_2$ is $C_4-C_7$-alkylene, especially pentylene.

Preferred embodiments of the invention relate to the above compounds of formula IA and IB wherein at least one of $R_2$, $R_3$, $R_4$ and $R_5$ is hydrogen. Preferred are the above compounds wherein $R_5$ is hydrogen, and further wherein $R_4$ and $R_5$ are hydrogen.

The invention relates in particular to the novel compounds itemized in the examples and to the manners of preparation described therein.

The invention further relates to methods for the preparation of the compounds according to the invention. The preparation of compounds of the formula I is, for example, characterized in that, a) for the manufacture of compounds of the formula I in which R is hydrogen, in a compound of the formula IIa

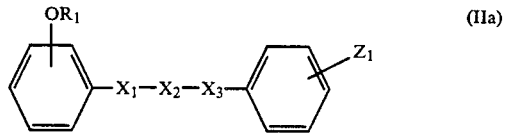

(IIa)

or a salt thereof in which $Z_1$ is a radical which can be converted into the variable —C(=NH)—NH—R, $Z_1$ is converted into the variable —C(=NH)—NH—R, or b) a compound of the formula IIIa

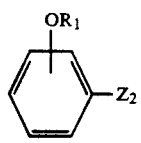

or a salt thereof is reacted with a compound of the formula IIIb

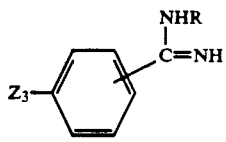

or a salt thereof in which $Z_2$ is a group of the formula $-X_1-X_2-Z_4$ and $Z_3$ is $-Z_5$, or $Z_2$ is $-Z_5$ and $Z_3$ is a group of the formula $Z_5-X_2-X_3-$, wherein one of the radicals $Z_4$ and $Z_5$ is hydroxy or mercapto and the other is hydroxy, mercapto or reactive esterified hydroxy, and, if desired, a compound of the formula I or a salt thereof obtainable according to the process or in another manner is converted into another compound or a salt thereof according to the invention, a free compound of the formula I obtainable according to the process is converted into a salt, a salt obtainable according to the process is converted into the free compound of the formula I or into another salt, or a mixture of isomers obtainable according to the process is resolved and the desired compound is isolated.

Salts of starting materials which contain at least one basic centre, for example of the formula IIa, are appropriate acid addition salts, while salts of starting materials which contain an acid group are present as salts with bases.

A radical $Z_1$ which can be converted into the variable $-C(=NH)-NH-R$ is, for example, (lower) alkoxy-iminocarbonyl or halogeno-iminocarbonyl [Halogeno$-C(=NH)-$].

Reactive esterified hydroxy (e.g. $Z_4$ or $Z_5$) is, in particular, hydroxy esterified with a strong inorganic acid or organic sulfonic acid, and is, for example, halogen, such as chlorine, bromine or iodine, sulfonyloxy, such as hydroxysulfonyloxy, halosulfonyloxy, such as, fluorosulfonyloxy, ($C_1$-$C_7$-)alkanesulfonyloxy which, if desired, is substituted, for example, by halogen, such as, methane- or trifluoromethanesulfonyloxy, ($C_5$-$C_7$-)cycloalkanesulfonyloxy, such as, cyclohexanesulfonyloxy, or benzenesulfonyloxy which, if desired, is substituted, for example by ($C_1$-$C_7$-)alkyl or halogen, such as, p-bromobenzene- or p-toluenesulfonyloxy.

The reactions described in the variants above and below are carried out in a manner known per se, for example in the absence or in the customary manner in the presence of a suitable solvent or diluent or a mixture thereof, the reaction being carried out, according to need, with cooling, at room temperature or with warming, for example in a temperature range from about $-80°$ C. up to the boiling point of the reaction medium, preferably from about $-10°$ C. to about $+180°$ C., and, if necessary, in a closed vessel, under pressure, in an inert gas atmosphere and/or under anhydrous conditions.

Process a)

Alkoxy-iminocarbonyl is, for example $C_1$-$C_4$alkoxy-iminocarbonyl such as methoxy- or ethoxy-iminocarbonyl, whereas halogeno-iminocarbonyl is, for example chloro-iminocarbonyl.

Preferably, those compounds of the formula IIa are employed in which $Z_1$ is $C_1$-$C_4$alkoxy-iminocarbonyl such as methoxy- or ethoxy-iminocarbonyl. The reaction is preferably carried out by reacting with ammonia and using an acid resulting in the corresponding acid addition salt of the product. As acids are used, for example, inorganic acids, such as mineral acids, for example sulfuric acid, a phosphoric or hydrohalic acid, or with organic carboxylic acids, such as ($C_1$-$C_4$)alkanecarboxylic acids which, for example, are unsubstituted or substituted by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as ($C_1$-$C_4$)alkane- or arylsulfonic acids which are unsubstituted or substituted, for example, by halogen, for example methane- or toluenesulfonic acid. Preferred acids are hydrohalic acids, especially hydrochloric acid, organic sulfonic acids, especially methanesulfonic acid, or dicarboxylic acids, especially maleic acid.

Process b)

Preferably, those compounds of the formulae IIIa and IIIb are employed in which $Z_2$ is a group of the formula $-X_1-X_2-Z_4$, wherein $Z_4$ is reactive esterified hydroxy, preferably halogen, especially bromine, and $Z_3$ is hydroxy or mercapto.

The reaction is carried out preferably in the presence of a base.

Suitable bases are, for example, alkali metal hydroxides, hydrides, amides, alkanolates, carbonates, triphenylmethylides, di(lower alkyl)amides, aminoalkylamides or lower alkyl silylamides, or naphthaleneamines, lower alkylamines, basic heterocycles, ammonium hydroxides, and also carbocyclic amines. Examples which may be mentioned are sodium hydroxide, sodium hydride, sodium amide, sodium (m)ethoxide, potassium tert-butoxide, potassium carbonate, lithium triphenylmethylide, lithium diisopropylamide, potassium 3-(aminopropyl)amide, potassiumbis(trimethylsilyl)amide, dimethylaminonaphthalene, di- or triethylamine, or ethyldiisopropylamine, N-methylpiperidine, pyridine, benzyltrimethylammonium hydroxide, 1,5-diazabicyclo[4.3.0]non-5-ene (DBN) and 1,8-diazabicyclo[5.4.0]undec-7-ene (DBU). Preferred is cesium carbonate.

The starting material can be prepared following methods known per se.

In order to prepare the starting material of the formula IIa, for example, a compound of the formula

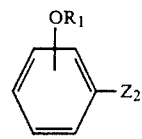

in which $Z_2$ preferably is a group of the formula $-X_1-X_2-Z_4$, wherein $Z_4$ preferably is reactive esterified hydroxy, is reacted with a compound of the formula

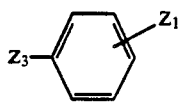
(IIc)

in which $Z_3$ preferably is hydroxy or mercapto, following the method as described in process b).

If one of variables $Z_2$ and $Z_4$ represents reactive esterified hydroxy, the other preferably represents hydroxy or mercapto.

A compound of the formula IIIb can be obtained, for example, by converting $Z_1$ of a compound of the formula (IIc) in which $Z_1$ is a radical which can be converted into the variable $-C(=NH)-NHR$ following the method as described in process a). Compounds of formulae (IIb) and (IIc) are known or can be prepared according to methods known per se. Preferably, $Z_2$ is a group of the formula $-X_1-X_2-Z_4$, wherein $Z_4$ is preferably reactive esterified hydroxy, such as chlorine or bromine, and $Z_3$ is hydroxy or mercapto. A corresponding compound of the formula IIc, wherein $Z_2$ is a group of the formula $-X_1-X_2-Z_4$ and $Z_4$ is preferably reactive esterified hydroxy, such as chlorine or bromine, can be obtained, for example, by reacting a compound of the formula $Z_4-X_2-Z_4$ (IId) with a compound of the formula

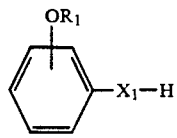
(IIe)

preferably in the presence of a base.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

A compound according to the invention which is obtainable by the process can be converted into another compound according to the invention in a manner known per se.

If R is hydrogen, the corresponding amidino group can be N-acylated accordingly. The acylation is carried out in a manner known per se using a suitable acylating agent. An example of a suitable acylating agent is a compound of the formula $Ac-Z_6$ (IIIa), where Ac denotes an acyl radical corresponding to the variable R, and $Z_6$ denotes in particular reactive activated hydroxyl. Appropriate hydroxyl can be activated, for example, by strong acids such as hydrohalic or carboxylic acid, for example by hydrochloric, hydrobromic acid, an optionally substituted, for example by halogen, alkanecarboxylic acid or by an acid of the formula $Ac-OH$, or by suitable activating or coupling reagents of the type detailed hereinafter, in particular in situ. $Ac-Z_6$ can furthermore represent an activated ester, where $Z_6$ denotes, in particular, cyanomethoxy, (4-)nitrophenoxy or polyhalogeno-, such as pentachloro-, -phenoxy. Activating and coupling reagents which can be employed are, in particular, carbodiimides, for example N,N'-di-$C_1$-$C_4$-alkyl- or N,N'-di-$C_5$-$C_7$-cycloalkyl-carbodiimide, such as diisopropylcarbodiimide or N,N'-dicyclohexylcarbodiimide, advantageously with the addition of an activating catalyst such as N-hydroxysuccinimide or optionally substituted, for example by halogen, $C_1$-$C_7$-alkyl or $C_1$-$C_7$-alkoxy, N-hydroxy-benzotriazole or N-hydroxy-5-norbornene-2,3-dicarboxamide, furthermore $C_1$-$C_4$-alkyl halogenoformate, for example isobutyl chloroformate, suitable carbonyl compounds, for example N,N-carbonyldiimidazole, suitable 1,2-oxazolium compounds, for example 2-ethyl-5-phenyl-1,2-oxazolium 3'-sulfonate or 2-tert-butyl-5-methyl-isoxazolium perchlorate, suitable acylamino compounds, for example 2-ethoxy-1-ethoxycarbonyl-1,2-dihydroquinoline, or suitable phosphoryl cyanamides or azides, for example diethylphosphoryl cyanamide or diphenylphosphoryl azide, furthermore triphenylphosphine disulfide or 1-$C_1$-$C_4$-alkyl-2-halogeno-pyridinium halides, for example 1-methyl-2-chloropyridinium iodide. $Z_6$ preferably denotes halogen such as chlorine or bromine, and $Ac-O-$.

If the compounds of the formula (I) or (IA) or (IB) contain unsaturated radicals, such as (lower)alkenyl groups, these can be converted into saturated radicals in a manner known per se. Thus, for example, multiple bonds are hydrogenated by catalytic hydrogenation in the presence of hydrogenation catalysts, suitable for this purpose being, for example, nickel, such as Raney nickel, and noble metals or their derivatives, for example oxides, such as palladium or platinum oxide, which may be applied, if desired, to support materials, for example to carbon or calcium carbonate. The hydrogenation may preferably carried out at pressures between 1 and about 100 at and at room temperature between about $-80°$ to about 200° C., in particular between room temperature and about 100° C. The reaction is advantageously carried out in a solvent, such as water, a lower alkanol, for example ethanol, isopropanol or n-butanol, an ether, for example dioxane, or a lower alkanecarboxylic acid, for example acetic acid.

The invention also relates to any novel starting materials and processes for their manufacture and their use.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. Racemic amidines (wherein $R_3$ represents hydrogen) can thus be resolved into their optical antipodes e.g. by fractional crystallization of a salt formed with an optically active acid.

Finally, the compounds of the invention are either obtained in the free form, or as a salt thereof.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to antagonize $LTB_4$ receptors, and for the treatment of a condition or syndrome responsive to the selective antagonism of $LTB_4$ receptors, comprising an effective amount of a pharmacologically active compound of the invention, alone or in combination, with one or more pharmaceutically acceptable carriers.

The novel pharmaceutical products contain, for example, from about 10% to about 80%, preferably from about 20% to about 60%, of the active compound. Examples of pharmaceutical products according to the invention for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated tablets.

The pharmacologically active compound of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for topical application e.g. to the skin and eyes are preferably aqueous solutions, ointments, creams or gels well-known in the art.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

In conjunction with another active ingredient, a compound of the invention may be administered either simultaneously, before or after the other active ingredient, either separately by the same or different route of administration or together in the same pharmaceutical formulation.

The invention further particularly relates to a method for the treatment of a condition or syndrome responsive to the selective antagonism of $LTB_4$ receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, osteoarthritis and late phase asthma; also for the treatment of pain and of ocular allergies and inflammations.

The dosage of active compound administered is dependent on the species of warm-blooded animal (mammal), the body weight, age and individual condition, and on the form of administration. A unit dosage for oral administration to a mammal of about 70 kg may contain e.g. between about 1 and about 1000 mg/kg per day of the active ingredient.

The following examples are intended to illustrate the invention and are not to be construed as being limitations thereon. Temperatures are given in degrees Centrigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1

To a suspension of 9.3 g (23.6 mmol) of ethyl 4-[5-(2-methoxyphenoxy)pentoxy] benzenecarboximidoate hydrochloride in 230 mL of ethanol cooled in an ice-bath is bubbled ammonia gas for 15 minutes. The resulting solution is stirred at room temperature overnight. The solvent is removed under reduced pressure and the residue dissolved in methanol and an equivalent of methanesulfonic acid added and the solution diluted with a large volume of ether. The crude salt produced is recrystallized from ethanol to give 4-[5-(2-methoxyphenoxy)pentoxy] benzenecarboximidamide monomethanesulfonate, m.p. 115°–117° C.

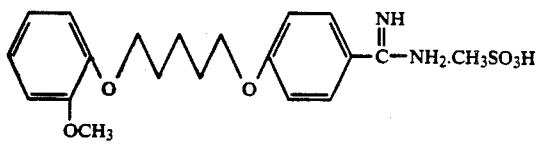

Similarly prepared are the hydrochloride salt, m.p. 89°–90° C., and the maleate salt, m.p. 163°–165° C.

The starting material can be prepared, for example as follows.

To a solution of 16.9 g (135 mmol) p-cyanophenol in 169 mL of dimethylformamide (DMF), cooled in an ice-bath is added in portions 6.5 g (135 mmol) sodium hydride (50% dispersion in oil). The reaction is stirred and allowed to warm-up to room temperature until no further hydrogen evolution is observed. The solution is then cooled in an ice-bath and a solution of 1-bromo-5-chloro-pentane 25 g (135 mmol) in 84 mL of dimethylformamide is added. The reaction is allowed to warm up to room temperature and stirred for 18 h. The reaction is then poured onto water and the resulting solid filtered off and dried to give 4-(5-chloropentoxy) benzonitrile, m.p. 52°–54° C.

To a solution of 32.7 g (146 mmol) of 4-(5-chloropentoxy) benzonitrile in 350 mL acetone is added 38.3 g (150 mmol) of sodium iodide in 230 mL of acetone. The reaction is heated to reflux and stirred overnight. The acetone is removed under reduced pressure and the residue partitioned between water and ether. The ethereal layer is dried, filtered and evaporated to give 4-(5-iodopentoxy) benzonitrile, m.p. 51°–54° C.

To a solution of 5.1 g (41 mmol) of guaiacol in 41 mL of DMF, cooled in an icebath, is added in portions, 20 g (41 mmole) of sodium hydride (50% dispersion in oil). The reaction is allowed to warm up to room temperature and stirred until no further hydrogen evolution is observed. The solution is then again cooled in an ice-bath and a solution of 13 g (41 mmol) 4-(5-iodopentoxy) benzonitrile in 82 mL DMF added. The reaction is allowed to warm up to room temperature and stirred for 18 h before pouring the mixture into water. The resulting solid is filtered off and dried to give 4-[5-(2-methoxyphenoxy)pentoxy] benzonitrile, m.p. 61°–63° C.

To a solution of 11.8 g (38 mmol) 4-[5-(2-methoxyphenoxy)pentoxy] benzonitrile in a mixture of 161 mL of methylene chloride and 6.8 mL of ethanol is bubbled hydrogen chloride gas for a period of 15 min. The reaction is then stirred at room temperature for 6 days. The solvents are removed under reduced pressure and the residue triturated with ether to give ethyl 4-[5-(2-methoxyphenoxy)pentoxy] benzenecarboximidoate hydrochloride, m.p. 114°–116° C.

EXAMPLE 2

In a way analogously as described in Example 1, the following compounds can be manufactured:

4-[5-(2,3-dimethoxyphenoxy)pentoxy]benzenecarboximidamide monomethanesulfonate, m.p.=163°–165° C.

4-[5-(2,6-dimethoxyphenoxy)pentoxy]benzenecarboximidamide monomethanesulfonate, m.p.=123°–126° C.

4-[5-[2-(1-methylethoxy)phenoxy]pentoxy]benzenecarboximidamide monomethanesulfonate, m.p.=102°–107° C.

4-[5-[2-(phenylmethoxy)phenoxy]pentoxy]benzenecarboximidamide monomethanesulfonate, m.p.=116°–123° C.

4-[5-(2-ethoxyphenoxy)pentoxy]benzenecarboximidamide monomethanesulfonate, m.p.=128°–129° C.

4-[5-(2-hexyloxyphenoxy)pentoxy]benzenecarboximidamide monomethanesulfonate, m.p.=129°–130° C.

4-[5-(5-fluoro-2-methoxyphenoxy)pentoxy]benzenecarboximidamide monomethanesulfonate, m.p.=130°–131° C.

4-[5-(4,5-difluoro-2-methoxyphenoxy)pentoxy]benzenecarboximidamide monomethanesulfonate, m.p. 140°–142° C. 4-[5-[4,5-difluoro-2-(1-methylethoxy)phenoxy]pentoxy]benzenecarboximidamide monomethanesulfonate, m.p.=136°–137° C.

3-methoxy-4-[5-(2-methoxyphenoxy)pentoxy]benzenecarboximidamide monomethanesulfonate, m.p.=140° C.

3-fluoro-4-[5-(2-methoxyphenoxy)pentoxy]benzenecarboximidamide monomethanesulfonate, m.p.=130° C.

3,5-dichloro-4-[5-(2-methoxyphenoxy)pentoxy]benzenecarboximidamide monomethanesulfonate, m.p.=124°–126° C.

3-chloro-4-[5-(2-methoxyphenoxy)pentoxy]benzenecarboximidamide monomethanesulfonate, m.p.=148°–149.5° C.

2-fluoro-4-[5-[2-(1-methylethoxy)phenoxy]pentoxy]benzenecarboximidamide monomethanesulfonate, m.p.=142°–144° C.

4-[4-(2-methoxyphenoxy)butoxy]benzenecarboximidamide monomethanesulfonate, m.p.=139°–140° C.

4-[6-(2-methoxyphenoxy)hexyloxy]benzenecarboximidamide monomethanesulfonate, m.p.=147°–148° C.

4-[4-[(2-methoxyphenoxy)methyl]phenylmethoxy]benzenecarboximidamide monomethanesulfonate, m.p.=182°–185° C.

4-[5-[5-fluoro-2-(1-methylethoxy)phenoxy]pentoxy]benzenecarboximidamide monomethanesulfonate, m.p.=94°–96° C.

4-[5-(4-fluoro-2-methoxyphenoxy)pentoxy]benzenecarboximidamide monomethanesulfonate, m.p.=129°–131° C.

4-[5-[4-fluoro-2-(1-methylethoxy)phenoxy]pentoxy]benzenecarboximidamide monomethanesulfonate, m.p. 124°–127° C.

4-[5-[4-(1,1,3,3-tetramethylbutyl)-2-methoxyphenoxy]pentoxy]benzenecarboximidamide hydrochloride.

EXAMPLE 3

A stirred, 0° C. solution of ethyl 4-[5-(2-phenylmethoxy)phenoxy]pentoxy]benzenecarboximidoate (320 mg, 0.71 mmol) in 8 mL anhydrous ethanol in a pressure tube is treated with anhydrous ammonia for 15 minutes. The pressure tube is sealed and heated to 100° C. for 45 minutes. Upon cooling and concentrating in vacuo, the resulting material is dissolved in methanol and an equivalent of methanesulfonic acid added and the solution diluted with a large volume of ether. The crude salt produced is recrystallized from ethanol to give 4-[5-[(2-phenylmethoxy)phenoxy]pentoxy]benzenecarboximidamide monomethanesulfonate, m.p. 116°–123° C.

The starting material, ethyl 4-[5-[(2-phenylmethoxy]phenoxy]pentoxy]benzenecarboximidoate, can be prepared, for example, as follows:

A stirred, 0° C. solution of 4-hydroxybenzonitrile (50.7 g, 426 mmol) in 1400 mL of dichloromethane and 75 mL anhydrous ethanol is treated with anhydrous hydrogen chloride gas (110 g) over 1.5 hours. This solution is stirred at room temperature for 64 hours and the resulting solids collected and washed with 500 mL diethyl ether and 2×1000 mL of ethyl acetate. The remaining solids (60.4 g) were dissolved in 1200 mL of water and the residual solids filtered. To the filtrate is added a solution of sodium hydroxide (12.57 g) in 150 mL water. The resulting white solid is filtered and washed with water to afford ethyl 4-hydroxybenzenecarboximidoate.

A stirred solution of ethyl 4-hydroxybenzenecarboximidoate (32.0 g, 194 mmol) in 250 mL anhydrous N,N-dimethylformamide is treated with cesium carbonate (75.7 g, 232 mmol) and 1,5-dibromopentane (89.1 g, 387 mmol) and heated at 70° for 1.5 hours. After cooling to room temperature, the reaction is filtered and the resulting filtrate concentrated in vacuo to afford a yellow oil (85.7 g). This material is purified by chromatography on silica gel (850 g) with 10–60% ethyl acetate/hexanes as the eluent to afford ethyl 4-[5-bromopentoxy]benzenecarboximidoate as a colorless oil.

A stirred solution of 2-phenylmethoxyphenol (200 mg, 1 mmol) in 5 mL anhydrous N,N-dimethylformamide is treated with cesium carbonate (330 mg, 1 mmol) and ethyl 4-[5-bromopentoxy]benzenecarboximidoate (300 mg, 1 mmol) and stirred at R.T. for 24 h. The reaction is poured into water and the solids filtered off and dried in vacuo to afford ethyl 4-[5-[(2-phenylmethoxy)phenoxy]pentoxy]benzenecarboximidoate m.p. 77°–79° C.

EXAMPLE 4

In a way analogous as described in Example 3, the following compounds can be manufactured:

4-[5-[(2-methoxy-4-(1-methylethoxy)phenoxy)]pentoxy]benzenecarboximidamide monohydrochloride.

4-[5-[(2-methoxy-4-(phenylmethoxy)phenoxy)]pentoxy]benzenecarboximidamide monohydrochloride.

4-[5-[4-(cyclohexylmethoxy)-2-methoxyphenoxy]-pentoxy]benzenecarboximidamide monohydrochloride.

4-[5-[2-methoxy-4-(2-methylpropoxy)phenoxy)pentoxy]benzenecarboximidamide monohydrochloride.

4-[5-(2-methoxy-5-methylphenoxy)pentoxy]benzenecarboximidamide monomethanesulfonate, 4-[5-(4-bromo-2-methoxyphenoxy)pentoxy]benzenecarboximidamide monohydrochloride, m.p.=85°–86° C.

4-[5-[(2-methoxyphenyl)thio]pentoxy]benzenecarboximidamide monomethanesulfonate, m.p.=125°–127° C.

4-[[5-(2-methoxyphenoxy)pentoxy]thio]benzenecarboximidamide monomethanesulfonate, m.p.=95°–98° C.

EXAMPLE 5

Ethanol (2 B anhydrous, 16.5 L) is cooled with an ice-salt bath to 0° C. Anhydrous hydrogen chloride is introduced until the solution is saturated (~8 hours). At this time the internal temperature is 5° C. To this is added 4-[5-(2-methoxyphenoxy)pentoxy]benzonitrile (1.64 kg, 5.26 mol) as a solid within a period of 10 minutes. At this point additional hydrogen chloride is introduced to maintain saturation at 5° C. for another 8 hours. Almost complete solution is achieved and the color is yellow. The reaction mixture is stirred for a total of 84 hours and the temperature range maintained is 5°–10° C. The resulting slurry is diluted with diethyl ether (52 L) to complete precipitation. The slurry is stirred for 1 hours and filtered. The filter cake is washed with diethyl ether (3×4 L) and air-dried for ½ hour to yield ethyl 4-[5-(2-methoxyphenoxy)pentoxy]benzenecarboximidate hydrochloride which is used directly in the next step.

Ethyl 4-[5-(2-methoxyphenoxy)pentoxy]benzenecarboximidate hydrochloride (from the previous step) is dissolved in ethanol (2 B anhydrous, 23 L) and the suspension is cooled in an ice-salt bath to 5° C. At this time anhydrous ammonia gas is introduced in a continuous stream added until saturation occurs (~4 hours). After stirring overnight, the temperature is approximately 15° C. Ammonia gas is again bubbled in a slow stream for 8 hours at 5° C. and the reaction proceeds for a total of another 24 hours. The temperature is allowed to rise to 20° C. and the procedure is repeated for an additional 24 hours at which time the reaction is complete. The solvent is then stripped in vacuo (65° C., 3 Torr) and the solid residue is taken up in hydrochloric acid (6.0N, 12 L). The suspension is stirred for 3 hours, filtered and the filter cake is washed with water (5×2 L) and air-dried overnight.

This crude hydrochloride salt is suspended in water (21 L) and the solution is cooled to 5° C. The pH is then adjusted to 12.3 with aqueous sodium hydroxide solution (2.0N, 2.9 L). The resulting suspension is stirred for 4 hours and the solid is filtered, washed with water (4×4 L) and air-dried overnight. Further drying is achieved in vacuo (49° C., 3 Torr) for 72 hours to yield 4-[5-(2-methoxyphenoxy)pentoxy]benzenecarboximidamide, m.p. 96°–98° C. HPLC indicates a purity >99.8%.

The starting material is prepared as follows:

Guiacol (1.06 kg, 8.53 mol) is dissolved in acetonitrile (17 L) and to this solution is added sequentially powdered anhydrous potassium carbonate (1.19 kg, 8.63 mol) and 1-bromo-5-chloropentane (1.59 kg, 8.57 mol). This suspension is then refluxed for 24 hours, cooled to 40° C. and filtered. The filtrate is concentrated in vacuo (55° C., 3 Torr) to give 2.0 kg of an oil which is dissolved in hexane (16 L), cooled in an ice bath with stirring and filtered to remove dimeric material. The filtrate is concentrated in vacuo (50° C., 3 Torr) to yield an oil. This material is subjected twice to distillation in a wiping-film distillation apparatus to remove starting alkylating agent and residual dimeric material and obtain 1-(5-chloropentoxy)-2-methoxybenzene which is 95% pure by glc analysis.

4-Cyanophenol (742 g, 6.23 mol) is dissolved in dimethyl sulfoxide (7.30 L) and to this solution is added powdered anhydrous potassium carbonate (883 g, 6.30 mol), potassium iodide (1.05 kg, 6.30 mol) and finally 1-(5-chloropentoxy)-2-methoxybenzene (1.44 kg, 6.29 mol). This suspension is heated at 80°–82° C. for 7 hours and the heating bath is then removed. After stirring overnight at room temperature, the mixture is poured onto cold water (29 L) and the product precipitates. This mixture is then extracted with ethyl acetate (3×20 L). The organic extracts are washed with potassium hydroxide solution (0.50N, 4×8 L), brine (2×10 L), dried over anhydrous sodium sulfate, filtered and concentrated in vacuo to yield a yellow oil which crystallizes on standing. This is then dissolved in 2-propanol (5.6 L) with warming and the resulting solution is filtered gravimetrically, washing the funnel with 1.2 L of hot 2-propanol. The combined filtrate is cooled to 10° C. in an ice bath and the solid mass is broken up and filtered. The filter cake is washed with 2-propanol (2×800 mL), dried in vacuo to give 4-[5-(2-methoxyphenoxy)pentoxy]benzonitrile, m.p. 66°-68° C. which is >99.5% pure by glc analysis.

EXAMPLE 6

4-[5-(2-Methoxyphenoxy)pentoxy]benzenecarboximidamide is dissolved in ethanol (2 B anhydrous, 9.6 L) with warming to 55° C. and this solution is filtered into a 10 gallon resin flask. The filtrate whose temperature is now 50° C. is admixed with a warm (~45° C.), filtered solution of maleic acid (0.488 kg, 4.20 mol) in 2 B anhydrous ethanol (4.15 L) rapidly. The product precipitates almost immediately and temperature rises to approximately 60°-65° C. The mixture is cooled to 5° C. with an ice bath for 2 hours and then filtered. The filter cake is washed with 2 B anhydrous ethanol (2×1 L) and then dried in vacuo (71° C., 3 mm Hg) for 16 hours to yield 4-[5-(2-methoxyphenoxy)pentoxy]benzenecarboximidamide (Z)-2-butenedioate, m.p. 163°-165° C.

This material is suspended in absolute ethanol (8.9 L) and the suspension is heated to 65° C. At this point water (0.89 L) is added and the internal temperature is raised to 74° C. to effect complete solution. The heating bath is removed and the product crystallizes. The thick suspension is cooled to 5° C. for 2 hours and filtered. The filter cake is washed with ethanol (3×500 mL) and dried in vacuo (71° C., 3 Torr) for 48 hours to yield 4-[5-(2-methoxyphenoxy)pentoxy]benzenecarboximidamide (Z)-2-butenedioate, m.p. 164°-166° C. (dec). HPLC analysis indicates a purity >99.8%.

EXAMPLE 7 a) Preparation of 10,000 tablets each containing 20 mg of the active ingredient, for example, 4-[5-(2-methoxyphenoxy)pentoxy]benzenecarboximidamide (Z)-2-butenedioate:

| active ingredient | 200.00 g |
| Lactose | 2,535.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10-100 mg of one of the other compounds disclosed and exemplified herein.

b) Preparation of 1,000 capsules each containing 40 mg of the active ingredient, for example, 4-[5-(2-methoxyphenoxy)pentoxy]benzenecarboximidamide (Z)-2-butenedioate:

| active ingredient | 40.00 g |
| Lactose | 177.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10-100 mg of the other compounds disclosed and exemplified herein.

What is claimed is:

1. A compound of the formula

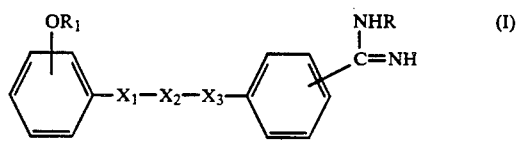

wherein the C(C=NH)—NHR group may be in tautomeric or isomeric form,

R is hydrogen or an acyl radical which is derived from an organic carbonic acid, an organic carboxylic acid, a sulfonic acid, or a carbamic acid;

$R_1$ is a substituent selected from an aliphatic hydrocarbon radical, an araliphatic hydrocarbon radical and a cycloaliphatic hydrocarbon radical;

$X_1$ and $X_3$, independently of one another, are oxygen (—O—) or sulphur (—S—); and $X_2$ is a divalent aliphatic hydrocarbon radical which may be interrupted by an aromatic radical; wherein the phenyl rings of formula I may be, independently of one another, further substituted by one or more substituents selected from halogen, trifluoromethyl, an aliphatic hydrocarbon radical, hydroxy, and hydroxy which is etherified by an aliphatic, araliphatic or cycloaliphatic alcohol or which is esterified by an aliphatic or araliphatic carboxylic acid;

wherein aryl in the above definitions may be, independently of one another, further substituted by one or more substituents selected from halogen, trifluoromethyl, an aliphatic hydrocarbon radical, hydroxy, and hydroxy which is etherified by an aliphatic, araliphatic or cycloaliphatic alcohol or which is esterified by an aliphatic or araliphatic carboxylic acid; and wherein a cycloaliphatic hydrocarbon radical may be substituted by an aliphatic radical; or a pharmaceutically acceptable salt thereof.

2. A compound according to claim 1 wherein R is hydrogen, ($C_1$-$C_{12}$-)alkoxycarbonyl or ($C_2$-$C_{12}$-)alkenyloxycarbonyl, each of which is unsubstituted or substituted by phenyl, naphthyl, indanyl or fluorenoyl, or is ($C_3$-$C_7$-)cycloalkoxycarbonyl being unsubstituted or mono- or polysubstituted by lower alkyl, or is lower alkanoyl or phenyl-lower alkanoyl, or is benzoyl, naphthoyl, indanoyl or fluorenoyl, or is ($C_1$-$C_7$-)alkanesulfonyl, phenyl-($C_1$-$C_7$-)alkanesulfonyl, ($C_3$-$C_7$-)cycloalkanesulfonyl, or phenylsulfonyl, or is aminocarbonyl which is substituted by lower alkyl, phenyl-lower alkyl or phenyl;

$R_1$ is lower alkyl, lower alkenyl, lower alkynyl, phenyl-lower alkyl, phenyl-lower alkenyl, phenyl-lower alkynyl, ($C_3$–$C_7$-)cycloalkyl, ($C_3$–$C_7$-)cycloalkenyl, ($C_3$–$C_7$)-cycloalkyl-lower alkyl or ($C_3$–$C_7$)-cycloalkenyl-lower alkyl;

$X_1$ and $X_3$, independently of one another, are O or S;

$X_2$ is lower alkylene, lower alkylene-phenylene-lower alkylene or lower alkylene-naphthylene-lower alkylene;

wherein the phenyl rings of formula I may be, independently of one another, further substituted by one or more substituents selected from halogen, trifluoromethyl, lower alkyl, lower alkenyl, lower alkynyl, hydroxy, lower alkoxy, lower alkenyloxy, phenyl-lower alkoxy, lower alkanoyloxy, lower alkenoyloxy and phenyl-lower alkanoyloxy; wherein the aromatic radicals in the above definitions may be, independently of one another, substituted by one or more substituents selected from halogen, trifluoromethyl, lower alkyl, lower alkenyl, lower alkynyl, hydroxy, lower alkoxy, lower alkenyloxy, phenyl-lower alkoxy, cyclohexyl-lower alkoxy, lower alkanoyloxy, lower alkenoyloxy and phenyl-lower alkanoyloxy; or a pharmaceutically acceptable salt thereof.

3. A compound according to claim 1 wherein R is hydrogen, $C_1$–$C_{12}$-alkoxy-carbonyl, $C_2$–$C_5$-alkanoyl, phenyl-$C_2$–$C_5$-alkanoyl, benzoyl which is unsubstituted or substituted by halogen, trifluoromethyl, $C_1$–$C_7$-alkyl, or $C_1$–$C_7$-alkoxy, $C_3$–$C_6$-cycloalkylcarbonyl which is unsubstituted or substituted by $C_1$–$C_7$-alkyl, or is benzoyl, naphthtoyl, indanoyl or fluorenoyl, or is $C_1$–$C_7$alkanesulfonyl, phenyl-$C_1$–$C_7$alkanesulfonyl, $C_3$–$C_7$-cycloalkanesulfonyl, or phenylsulfonyl, or is aminocarbonyl which is substituted by $C_1$–$C_7$-alkyl, phenyl-$C_1$–$C_7$-alkyl or phenyl;

$R_1$ is $C_1$–$C_7$-alkyl, phenyl-$C_1$–$C_7$-alkyl or $C_3$–$C_6$-cycloalkyl;

$X_1$ and $X_3$ each are —O—, or furthermore are, independently of one another —O— or —S—;

$X_2$ is $C_2$–$C_7$-alkylene or $C_2$–$C_4$-alkylene-phenylene-$C_2$–$C_4$-alkylene;

wherein phenyl in the above definitions is unsubstituted or, furthermore, independently of one another, substituted by one or more substituents selected from halogen, trifluoromethyl, $C_1$–$C_7$-alkyl, and $C_1$–$C_7$-alkoxy; or a pharmaceutically acceptable salt thereof.

4. A compound according to claim 1 wherein —O—$R_1$ is located in position 2 (ortho) of the corresponding phenyl ring with respect to —$X_1$—; and —C(=NH)—NH—R is located in position 4 (para) of the corresponding phenyl ring with respect to —$X_3$—; or a pharmaceutically acceptable salt thereof.

5. A compound according to claim 1 of formula IA

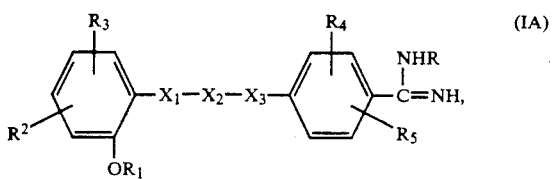

wherein the C(=NH)—NHR group may be in tautomeric or isomeric form, R is hydrogen, $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl, or $C_1$–$C_4$-alkoxy, $C_3$–$C_6$-cycloalkylcarbonyl which is unsubstituted or substituted by $C_1$–$C_4$-alkyl;

$R_1$ is $C_1$–$C_4$-alkyl, phenyl-$C_1$–$C_4$-alkyl, $C_3$–$C_6$-cycloalkyl;

$R_2$, $R_3$, $R_4$ and $R_5$, independently of one another, are hydrogen, halogen, $C_1$–$C_4$-alkoxy, or $C_1$–$C_4$-alkyl;

$X_1$ and $X_3$ are —O—;

$X_2$ is $C_4$–$C_7$-alkylene or $C_2$–$C_4$-alkylene-phenylene-$C_2$–$C_4$-alkylene; or a pharmaceutically acceptable salt thereof.

6. A compound according to claim 5 of formula IA wherein R is hydrogen;

$R_1$ is $C_1$–$C_4$-alkyl, phenyl-$C_1$–$C_4$-alkyl, $C_3$–$C_6$-cycloalkyl;

$R_2$, $R_3$, $R_4$ and $R_5$, independently of one another, are hydrogen, halogen, $C_1$–$C_4$-alkoxy, or $C_1$–$C_4$-alkyl;

$X_1$ and $X_3$ are —O—;

$X_2$ is $C_4$–$C_7$-alkylene or $C_2$–$C_4$-alkylene-phenyl-$C_2$–$C_4$-alkylene; or a pharmaceutically acceptable salt thereof.

7. A compound according to claim 5 of formula IA wherein R is $C_1$–$C_4$alkanesulfonyl, phenyl-$C_1$–$C_4$-alkanesulfonyl, $C_3$–$C_7$-cycloalkane-sulfonyl, or phenylsulfonyl, or is aminocarbonyl which is substituted by $C_1$–$C_4$-alkyl, phenyl-$C_1$–$C_4$-alkyl or phenyl;

$R_1$ is $C_1$–$C_4$-alkyl, phenyl-$C_1$–$C_4$-alkyl, $C_2$–$C_6$-cycloalkyl;

$R_2$, $R_3$, $R_4$ and $R_5$, independently of one another, are hydrogen, halogen, $C_1$–$C_4$-alkoxy or $C_1$–$C_4$-alkyl;

$X_1$ and $X_3$ are —O—;

$X_2$ is $C_4$–$C_7$-alkylene or $C_2$–$C_4$-alkylene-phenyl-$C_2$–$C_4$-alkylene; or a pharmaceutically acceptable salt thereof.

8. A compound according to claim 5 of formula IA wherein

R is hydrogen;

$R_1$ is $C_1$–$C_4$-alkyl or phenyl-$C_1$–$C_4$-alkyl;

$R_2$ is hydrogen or $C_1$–$C_4$-alkoxy;

$R_3$ is hydrogen or halogen;

$R_4$ and $R_5$, independently of one another are hydrogen, halogen or $C_1$–$C_4$-alkoxy;

$X_1$ and $X_3$ are —O—;

$X_2$ is $C_4$–$C_7$-alkylene; or a pharmaceutically acceptable salt thereof.

9. A compound according to claim 8 wherein $R_4$ and $R_5$ are hydrogen.

10. A compound according to claim 5 of formula IA wherein R is $C_1$–$C_{12}$-alkoxycarbonyl, phenyl-$C_1$–$C_4$-alkoxycarbonyl, $C_2$–$C_5$-alkanoyl, benzoyl which is unsubstituted or substituted by halogen, trifluoromethyl, $C_1$–$C_4$-alkyl, or $C_1$–$C_4$-alkoxy, $C_3$–$C_6$-cycloalkylcarbonyl which is unsubstituted or substituted by $C_1$–$C_4$-alkyl; $R_1$ is $C_1$–$C_4$-alkyl or phenyl-$C_1$–$C_4$-alkyl; $R_2$ is hydrogen, halogen or $C_1$–$C_4$-alkoxy; $R_3$ is hydrogen or halogen; $R_4$ and $R_5$, independently of one another, are hydrogen, halogen, or $C_1$–$C_4$-alkoxy; $X_1$ and $X_3$ are —O—; $X_2$ is $C_4$–$C_7$-alkylene; or a pharmaceutically acceptable salt thereof.

11. A compound according to claim 1 of formula IB

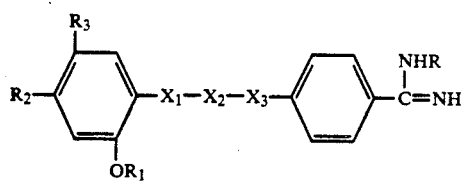 (IB)

wherein the C(=NH)—NHR group may be in tautomeric or isomeric form, R is hydrogen; $R_1$ is $C_1$-$C_4$-alkyl; $R_2$ and $R_3$, independently of one another, are hydrogen or halogen; $X_1$ and $X_3$ are —O—; $X_2$ is $C_4$-$C_7$-alkylene; or a pharmaceutically acceptable salt thereof.

12. A compound according to claim 5 which is 4-[5-(2-methoxyphenoxy)pentoxy]benzenecarboximidamide or a pharmaceutically acceptable salt thereof.

13. A compound according to claim 5 which is 4-[5-(5-fluoro-2-methoxyphenoxy)pentoxy]benzenecarboximidamide or a pharmaceutically acceptable salt thereof.

14. A compound according to claim 5 which is 4-[5-(4,5-difluoro-2-methoxyphenoxy)pentoxy]benzenecarboximidamide or a pharmaceutically acceptable salt thereof.

15. A compound according to claim 5 which is 4-[5-(2,6-dimethoxyphenoxy)pentoxy]benzenecarboximidamide or a pharmaceutically acceptable salt thereof.

16. A compound according to claim 5 which is 4-[5-[2-(phenylmethoxy)phenoxy]pentoxy]benzenecarboximidamide or a pharmaceutically acceptable salt thereof.

17. A pharmaceutical composition suitable for the treatment of a condition or syndrome responsive to the selective antagonism of $LTB_4$ receptors in mammals comprising an effective $LTB_4$ antagonizing amount of a compound of claim 1 or a pharmaceutically acceptable salt thereof and a carrier.

18. A pharmaceutical composition suitable for the treatment of rheumatoid arthritis, osteoarthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, or late phase asthma in mammals comprising an effective amount of a compound of claim 5 or a pharmaceutically acceptable salt thereof and a carrier.

19. A method for the treatment of a condition or syndrome responsive to the selective antagonism of $LTB_4$ receptors which comprises administering to a mammal in need thereof an effective $LTB_4$ receptors antagonizing amount of a compound according to claim 1 or a pharmaceutically acceptable salt thereof of a said compound and a carrier.

20. A method for the treatment of rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, ocular allergy and inflammation, or late phase asthma in mammals which comprises administering to a mammal in need thereof an effective amount of a compound according to claim 1 or a pharmaceutically acceptable salt thereof of a said compound and a carrier.

21. A method for the treatment of pain and osteoarthritis in mammals which comprises administering to a mammal in need thereof an effective analgesic amount of a compound according to claim 1.

* * * * *